United States Patent [19]

Adachi et al.

[11] Patent Number: 5,614,374

[45] Date of Patent: Mar. 25, 1997

[54] GLYCEROL DEHYDROGENASE, PROCESS FOR ITS PRODUCTION AND ITS USE

[75] Inventors: Osao Adachi; Kazunobu Matsushita, both of Yamaguchi, Japan

[73] Assignee: Toyo Boseki Kabushiki Kaisha, Osaka, Japan

[21] Appl. No.: 225,328

[22] Filed: Apr. 8, 1994

Related U.S. Application Data

[62] Division of Ser. No. 19,676, Feb. 19, 1993, Pat. No. 5,346,819.

[30] Foreign Application Priority Data

Feb. 24, 1992 [JP] Japan ................................ 4-73568

[51] Int. Cl.$^6$ ................................ C12Q 1/32; C12Q 1/26; C12Q 1/00; C12Q 1/48
[52] U.S. Cl. ................................ 435/26; 435/25; 435/4; 435/15; 435/19; 435/183; 435/190; 435/119
[58] Field of Search ................................ 435/26, 25, 4, 435/190, 183, 15, 19, 119

[56] References Cited

U.S. PATENT DOCUMENTS

| | | | |
|---|---|---|---|
| 4,259,440 | 3/1981 | Gupta et al. | 435/26 |
| 4,576,913 | 3/1986 | Adachi et al. | 435/26 |
| 4,636,465 | 1/1987 | Itoh et al. | 435/26 |
| 4,994,382 | 2/1991 | Ameyama et al. | 435/119 |
| 5,346,819 | 9/1994 | Adachi et al. | 435/190 |

OTHER PUBLICATIONS

Minoru Ameyama et al., "Solubilization, Purification and Properties of Membrane–bound Glycerol Dehydrogenase from Gluconobacter Industrius," Agric. Biol. Chem. 49(4), pp. 1001–1010, 1985.

Osao Adachi et al., "Enzymatic Determination of Pyrroloquinoline Quinone with a Quinoprotein Glycerol Dehydrogenase," Agric. Biol. Chem. 52(8), pp. 2081–2082, 1988.

Edwin C. Webb, Enzyme Nomenclature, Acad. Press Inc., New York, pp. 20–21 & 54–59 (1984).

Primary Examiner—John Kight
Assistant Examiner—Louise N. Leary
Attorney, Agent, or Firm—Foley & Lardner

[57] ABSTRACT

Pyrroloquinoline quinone-dependent glycerol dehydrogenase is provided which requires no surfactant for its solubilization and stabilization. The glycerol dehydrogenase has the following properties:

(a) catalyzing the following reaction:

glycerol+electron acceptor→ glyceraldehyde+reduced electron acceptor, (b) optimum pH: pH 8–9,
(c) pH stability: stable at pH 7–11,
(d) optimum temperature: 20°–25° C,
(e) thermal stability: stable at a temperature of 30° C or less for 10 minutes at a pH of 7.0,
(f) molecular weight: 70,000 by gel filtration and SDS polyacrylamide gel electrophoresis,
(g) bound to pyrroloquinoline quinone as a prosthetic group,
(h) soluble and stable without the need of an ionic or non-ionic surfactant.

6 Claims, 6 Drawing Sheets

Optimum pH of GLDH

─○─ 50mM McB
─□─ 50mM KPB
─●─ 50mM Tris-HCl buffer
─▲─ 50mM Gly-NaOH buffer

Fig. 1

Optimum pH of GLDH

―○― 50mM McB
―□― 50mM KPB
―●― 50mM Tris-HCl buffer
―▲― 50mM Gly-NaOH buffer

Fig. 2 pH Stability of GLDH

―○― 50mM McB
―□― 50mM KPB
―●― 50 mM Tris-HCl buffer
―▲― 50mM Gly-NaOH buffer

Fig. 3

Optimum temperature of GLDH

Fig. 4

Thermal stability of GLDH

GLYCEROL DEHYDROGENASE, PROCESS FOR ITS PRODUCTION AND ITS USE

This application is a divisional of U.S. application Ser. No. 08/019,676, filed Feb. 19, 1993, now U.S. Pat No. 5,346,819.

FIELD OF THE INVENTION

The present invention relates to glycerol dehydrogenase, a process for its production and its use. The glycerol dehydrogenase according to the present invention with pyrroloquinoline quinone (PQQ) as a prosthetic group is much stabler than the dehydrogenase of the prior art, and does not need any surfactant for its solubilization and stabilization. The glycerol dehydrogenase according to the present invention is useful for highly sensitive quantitative determination of glycerol in a system comprising a sample which contains glycerol.

DESCRIPTION OF THE BACKGROUND

According to the prior art, quantitative determination of glycerol in a sample which uses glycerol dehydrogenase is conducted in line with the following equation:

Glycerol+NAD$^+$→Dihydroxyacetone+NADH (glycerol dehydrogenase)

In view of the disadvantage of utilizing the expensive coenzyme NAD$^+$ in this process, we the inventors of the present invention decided to develop a cheap and simple method for quantitatively determining glycerol, focusing on PQQ-dependent glycerol dehydrogenase which utilizes an artificial electron acceptor. The glycerol dehydrogenase includes the one already reported which is produced by acetic acid bacterium, Gluconobacter industrius IFO 3260 (Ameyama et al., Agric. Biol. Chem., 49 1001–1010, 1985). The enzyme is, however, a cell membrane-bound type, and thus its solubilization through separation from the cells and its stabilization requires the use of a certain surfactant which may cause errors in the measurement of glycerol. Further, the enzyme is a rather highly hydrophobic membrane enzyme, and therefore is unstable in an aqueous solvent system, requiring the addition of 10% glycerol thereto as a stabilizing agent, in addition to a surfactant. These facts indicate why the enzyme cannot be used for quantitative determination of glycerol.

SUBJECT MATTER OF THE INVENTION

With due consideration for the prior art mentioned above, we have conducted some trials to find PQQ-dependent glycerol dehydrogenase which eliminates the necessity of using a surfactant and glycerol for solubilization and stability of the enzyme.

The inventors of the present invention carried out diligent research in order to solve the problems referred to above, and as a result soluble glycerol dehydrogenase has been found from Pseudomonas sp. TE3493 (FERM BP-4169), leading to the accomplishment of the present invention. That is, the present invention is concerned with glycerol dehydrogenase which has the following properties:

(1) It catalyzes the following reaction:

Glycerol+Electron Acceptor→

Glyceraldehyde+Reduced Electron Acceptor (2) Optimum pH: pH 8–9
(3) pH stability: Stable at pH 7–11
(4) Optimum temperature: 20°–25° C.
(5) Thermal stability: Stable at a temperature of 30° C. or less for 10 minutes' reaction at a pH of 7.0,
(6) Molecular weight: 70,000 by gel filtration and SDS polyacrylamide gel electrophoresis.
(7) Contains pyrroloquinoline quinone as a prosthetic group.
(8) No surfactant needed for its solubilization and stabilization.

In addition, the present invention is concerned with a method of producing a novel glycerol dehydrogenase characterized by cultivating, in a nutrient medium, a strain belonging to the genus Pseudomonas and capable of producing the above-mentioned novel glycerol dehydrogenase and recovering the novel glycerol dehydrogenase from the culture. Furthermore, the present invention relates to a method for quantitative determination of glycerol which uses the novel glycerol dehydrogenase in a system comprising a sample to be analyzed for glycerol.

The enzyme of the present invention has the following properties:

(1) It catalyzes the following reaction:

Glycerol+Electron Acceptor→Glyceraldehyde+Reduced Electron Acceptor (2) Optimum pH: pH 8–9
(3) pH stability: Stable at pH 7–11
(4) Optimum temperature: 20°–25° C.
(5) Thermal stability: Stable at a temperature of 30° C. or less for 10 minutes' at a pH of 7.0,
(6) Molecular weight: 70,000 by gel filtration and SDS polyacrylamide gel electrophoresis.
(7) Contains pyrroloquinoline quinone as a prosthetic group.
(8) No surfactant needed for its solubilization and stabilization.

For the enzyme of this invention any source or origin such as animals, plants, microorganisms, etc. may be used so far as it is capable of producing the glycerol dehydrogenase having the above mentioned properties. Preferably there is used a microorganism of the genus Pseudomonas which is capable of producing the glycerol dehydrogenase having the above mentioned properties. More specific example is Pseudomonas sp. TE3493 which is a strain isolated from the soil and has the following physiological properties:

(a) Morphological characteristics:
  (1) Shape: Rods
  (2) Size: 1.0 μm in diameter by 2.0~2.5 μm in length
  (3) Motility: +
  (4) Morphological variety: −
  (5) Spores: −
  (6) Gram stain: − (negative)
  (7) Acid fast test: −
(b) Cultural characteristics:
  (1) Meat extract agar plate culture: the organism produces light brown clonies and no pigments after 48h-incubation at 30° C. Colonies are round, raised, entire and undulate, and show surface making such as smooth, oleaginous and transparent.
  (2) Meat extract agar slant culture: A growth rate is fast. Other characteristics are the same as the description in (1).

(3) Meat extract liquid culture: A growth rate is fast. The organism produces a small amount of precipitation.
(4) Meat extract and gelatin agar stab culture: Well growth is observed around top of the stab. Gelatin is not liquefized.
(5) Litmus milk liquid culture: No change in color is obserbed. Peptonization occured.

(c) Physiological characteristics:
(1) Nitrate reduction: −
(2) Denitrification: −
(3) MR test: −
(4) VP test: −
(5) Indole production: −
(6) $H_2S$ production: −
(7) Hydrolysis of starch: −
(8) Citrate used as a carbon source: +(koser's medium), +(Christensen's medium)
(9) Nitrogen source used for growth:
   ammonium salts: +
   nitrate salts: −
(10) Pigment production: −
(11) Urease: −
(12) Oxidase: +
(13) Catalase: +
(14) β-Galactosidase: −
(15) Arginine dihydrolase: +
(16) Lysine decarboxylase: −
(17) Ornithine decarboxylase: −
(18) Tryptophan deaminase: −
(19) β-Glucosidase: −
(20) Growth: Growth at pH 5.0 to pH 10.0(pH) and at 20° C. to 37° C. (temperature). No growth at 42° C.
(21) Growth aerobically or anaerobically: Aerobically
(22) 0-F test: 0 (oxidation)
(23) Acid production from:

| | |
|---|---|
| L-Arabinose | + |
| D-Glucose | + |
| D-Fructose | − |
| D-Galactose | + |
| D-Mannose | + |
| D-Xylose | − |
| D-Sorbitol | − |
| D-Mannitol | − |
| Inositol | − |
| L-Rhamnose | − |
| Saccharose | − |
| Mannose | − |
| Lactose | − |
| D-Melibiose | − |
| Amygdalin | − |
| Glycerol | − |
| Starch | − |

The test for the determination of the above physiological properties was performed mainly by the methods described in T. Haegawa "Biseibutsu No Bunrui To Dotei" (Classification and Identification of Microorganisms) (1985), Gakkai Shuppan Center. The classification and identification were performed by referring to "Bergey's Manual of Determinative Bacteriology", 8th edition and "Bergey's Manual of Systematic Bacteriology" (vol. 1).

From the above literatures and physiological properties the above microorganism has been determined to be of the genus Pseudomonas. Further this microorganism is identical in the various properties to *Pseudomonas putida*, but does not produce soluble fluorescent pigment. Therefore the microorganism has been named Pseudomonas sp. TE3493 and was deposited at Fermentation Research Institute, Patent Microorganism Depository under FERM BP-4169 on Jun. 10, 1991.

The enzyme according to the present invention may be prepared by a process which comprises cultivation in a nutrient medium of the above-mentioned glycerol dehydrogenase-producing bacteria, and recovery of glycerol dehydrogenase from the culture. The culture medium available for use in the cultivation of the glycerol dehydrogenase-producing bacteria includes all synthetic and natural media that contain appropriate amounts of carbon sources, nitrogen sources, inorganic substance and other requisite nutrients which may be utilized by the strain used. The carbon sources include glucose, glycerol, etc. As the nitrogen sources are used, for example, nitrogenous natural nutrients such as peptones, meat extracts and yeast extracts, or inorganic nitrogenous compounds such as ammonium chloride and ammonium citrate. Potassium phosphate, sodium phosphate, magnesium sulfate or the like may be used as the inorganic substance. Preferably glycerol is added to the culture medium as an agent to induce the production of glycerol dehydrogenase.

The cultivation is usually effected by shaking culture or aeration-stirring culture, where the cultivation temperature is 20°–40° C., preferably 25°–37° C. and the cultivation pH range is 5–9, preferably controlled to within the range of 7–8. The cultivation may be carried out also under other conditions so far as the strain used can grow under them. Satisfactory growth of the cells are established in a usual cultivation period of 1–10 days, and glycerol dehydrogenase is produced and accumulated in the cells.

Purification of the enzyme according to the present invention may be carried out by a conventional purification method. As an example, its extraction may be effected by any of ultrasonification, mechanical disruption, a French press, a surfactant, etc. The extracts may be further purified by salting out with ammonium sulfate, Glauber's salt or the like, by precipitation with a metal such as magnesium chloride or potassium chloride, by agglutination using protamine, polyethyleneimine or the like, or by ion-exchange chromatography which uses DEAE (diethylaminoethyl)-sepharose, CM (carboxymethyl)-sepharose or the like. The thus prepared crude enzyme solution or purified enzyme solution may be pulverized by, for example, spray drying or lyophilization. The enzyme may be used as an immobilized enzyme which is prepared by fixing it on an appropriate carrier.

Hereunder is explained a method for the determination of the activity of the novel glycerol dehydrogenase according to the present invention. To the reaction solution are added 0.7 ml of a 50 mM Tris—HCl buffer solution, 0.1 ml of a 0.1 M glycerol and the enzyme solution to a total volume of 0.9 ml. The mixture was preheated at 25° C. for 5 minutes, and 0.1 ml of a 0.1 M potassium ferricyanide was added thereto for the initiation of the reaction. The reaction is terminated by addition of 0.5 ml of ferric sulfate/Dupanol reagent thereto, after which 3.5 ml of distilled water is added thereto to a total volume of 5 ml. Then the mixture was allowed to stand at 25° C. for 30 minutes, followed by measurement of absorbance at 660 nm. A blank test is carried out in the same manner as the above-mentioned one, but adding distilled water instead of the enzyme solution. The activity of glycerol dehydrogenase is expressed with one unit (U) being defined as the enzyme activity which oxidizes 1 μmole of glycerol in 1 minute under the conditions specified above.

In addition, the present invention relates to a method for the quantitative determination of glycerol which uses a novel glycerol dehydrogenase in a system comprising a sample to be analyzed for glycerol.

The sample which contains glycerol includes food, serum, plasma, etc. The quantitative determination of glycerol which are contained in the sample may be carried out using glycerol dehydrogenase according to the present invention in the manner mentioned below. The decrease in the absorbance is measured using, for example, potassium ferricyanide as the electron acceptor, or the measurement of the decrease in the absorbance is carried out in the presence of 2,6—dichlorophenolindophenol and phenazine methosulfate. Alternatively, the quantitative determination may be conducted by measuring the formazan coupling dyestuff which is produced in the presence of phenazine methosulfate and nitrotetrazolium blue. Also the enzyme according to the present invention may be employed for the measurement of neutral fat in serum, plasma, etc. with advantages. That is, the neutral fat in these samples is decomposed into free fatty acids and glycerol by, for example, lipoprotein lipase, and the thus produced glycerol may be subjected to quantitative determination which uses glycerol dehydrogenase and utilizes the process mentioned above. Measurement of neutral fat according to the prior art involves a problem for diagnosing psychopaths and patients who are receiving dialysis treatment which is connected with free glycerol, but this problem is not encountered if the glycerol in the body fluids is eliminated or measured for its quantity before-hand with glycerol dehydrogenase according to the present invention, to enable the determination of the net neutral fat value.

The enzyme according to the present invention does not require the use of certain surfactants and glycerol for its solubilization and stabilization, so measurement errors caused by the objectionable use of the surfactant or by exogenous glycerol attributable to its use as a stabilizer in the enzyme preparation may be avoided.

BRIEF DESCRIPTION OF DRAWINGS

The present invention will be further explained by the following Examples and by referring to the accompanying drawings wherein.

EXAMPLE 1

In a 500 ml Sakaguchi flask there were placed 100 ml of a culture medium which contained 0.5% glycerol, 0.2% $NaNO_3$, 0.2% $(NH_4)_2SO_4$, 1% $K_2HPO_4$, 1% $KH_2PO_4$, 0.02% $MgSO_4.7H_2O$ and 0.05% yeast extracts, followed by autoclaving at 121° C. for 15 minutes. One loopful of cells of Pseudomonas sp. (FERM BP-4169) were inoculated in the medium as the inoculum, and a seed culture was prepared after a 24 hours' cultivation at 30° C. Then 6 l of the culture was transferred to a 10 l jar fermenter, after which autoclaving was effected at 121° C. for 15 minutes. After being allowed to cool, 100 ml of the culture was further cultivated at 300 rpm, an aeration rate of 2 l/min. and 30° C. for 30 hours. The culture was subjected to centrifugation to harvest the cells which were suspended in a 50 mM phosphate buffer solution. The resulting suspension was treated with a French press and centrifuged to obtain a supernatant. The thus prepared crude enzyme solution was fractionated by ammonium sulfate fraction, DEAE-cellulose chromatography, DEAE-Toyopearl chromatography, hydroxyapatite chromatography and gel filtration in the order mentioned. Thus was provided an enzyme preparation which has a specific activity of 15 U/mg.

The obtained glycerol dehydrogenase has the following properties:

(1) Catalyzing of the following reaction:

Glycerol+Electron Acceptor →

Glyceraldehyde+Reduced Electron Acceptor

The product from the glycerol was identified in the manner mentioned below.

The reaction product, which was yielded by the action of glycerol dehydrogenase upon glycerol in the presence of phenazine methosulfate and nitrotetrazolium blue, was developed by thin-layer chromatography utilizing acetone as the developing solvent. At the same time as this dihydroxyacetone and glyceraldehyde were developed as the standards, followed by spraying of p-anisidine and heating at 110° C. Comparison of color development and Rf values proved that the product was identical with glyceraldehyde.

(2) Electron acceptor

It utilized potassium ferricyanide, 2,6-dichlorophenolindophenol, Wurster's blue, nitrotetrazolium blue, etc.

(3) Km value

The Km value for glycerol was 2.45 mM.

(4) Optimum pH

Figure 1:
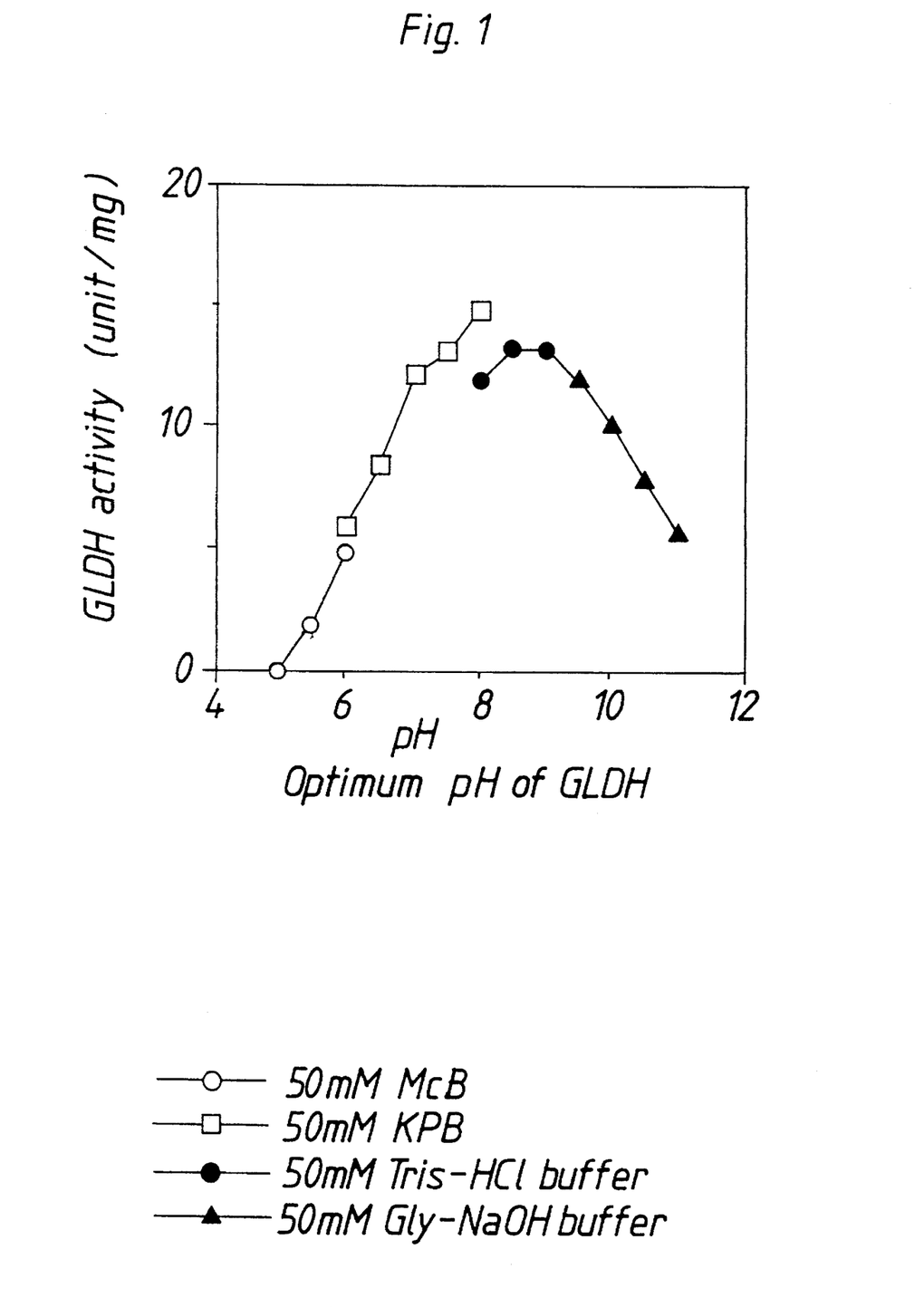
FIG. 1 is a graph showing the relationship between the reaction pH and the relative activity of the enzyme according to the present invention.

Determination was made of the enzyme activity in a 50 mM McIlvaine buffer solution (pH 5.0–6.0), a 50 mM K-phosphate buffer solution (pH 6.0–8.0), a 50 mM Tris-HCl buffer solution (pH 8.0–9.0) and a 50 mM glycine/NaOH buffer solution (pH 9.0–11.0). The results were as shown in FIG. 1, and the optimum pH was found to be 8.0–9.0.

(5) pH stability

Figure 2:
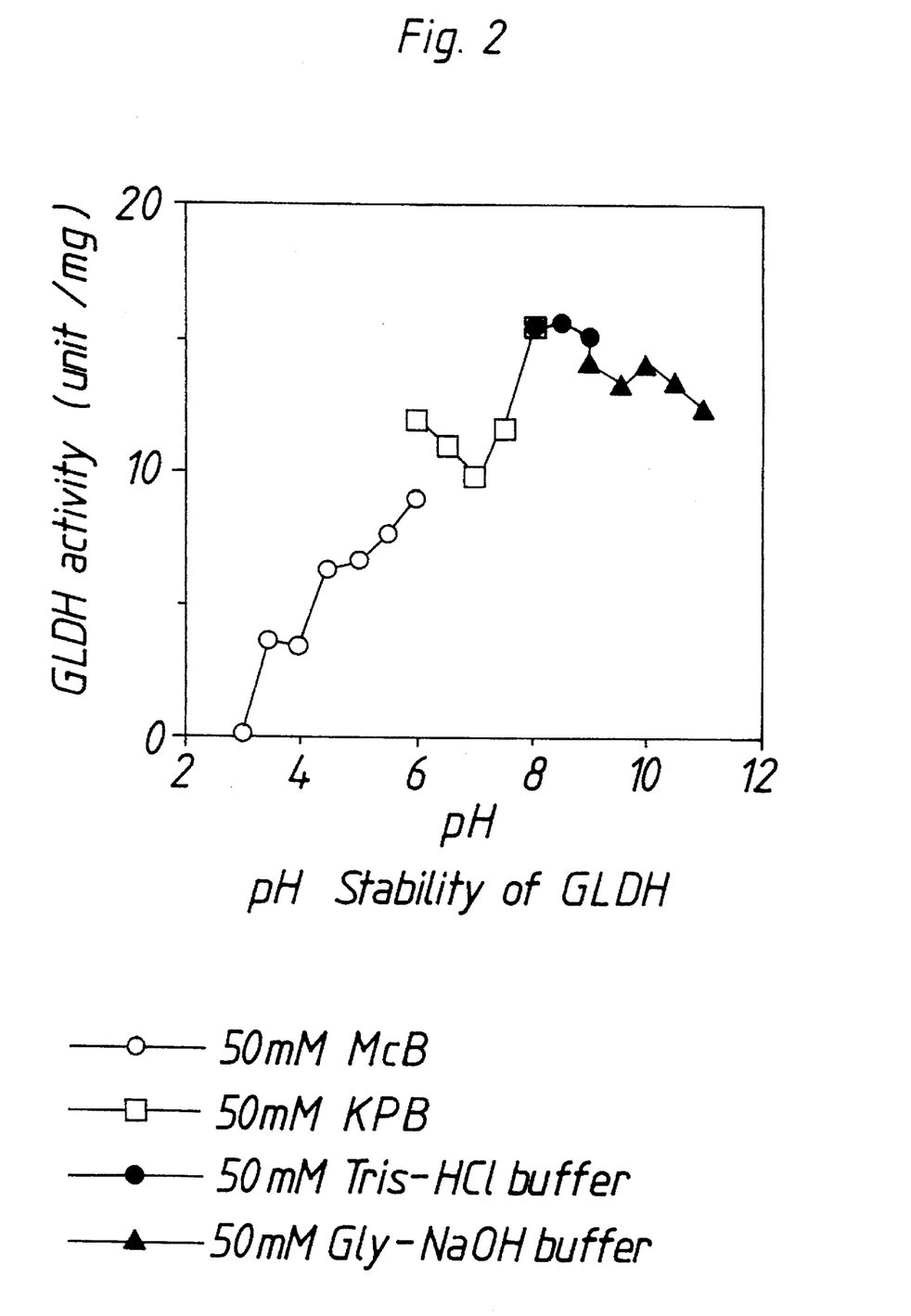
FIG. 2 is a graph showing the pH stability.

The enzyme according to the present invention was kept at 5° C. for one day, in each of the same buffer solutions as employed for the determination of the optimum pH, and then the residual activity was measured. The results are shown in FIG. 2, and the pH stability was observed at pH 7.0–11.0.

(6) Optimum temperature

Figure 3:
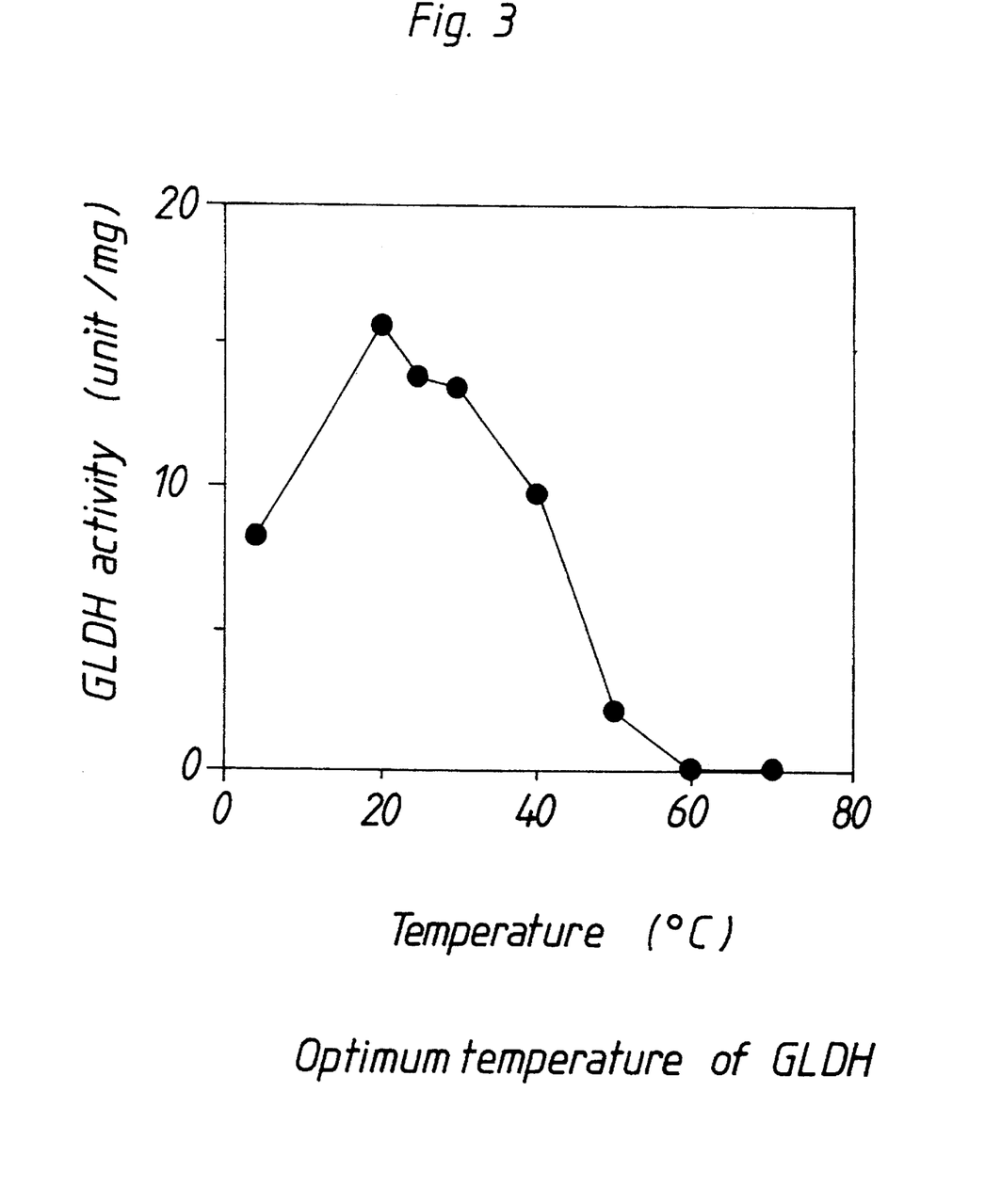
FIG. 3 is a graph showing the relationship between the reaction temperature and the relative activity of the enzyme according to the present invention.

The enzyme activity was measured at various temperatures. The results were as shown in FIG. 3, and the optimum temperature was found to be 20°–25° C.

(7) Thermal stability

Figure 4:
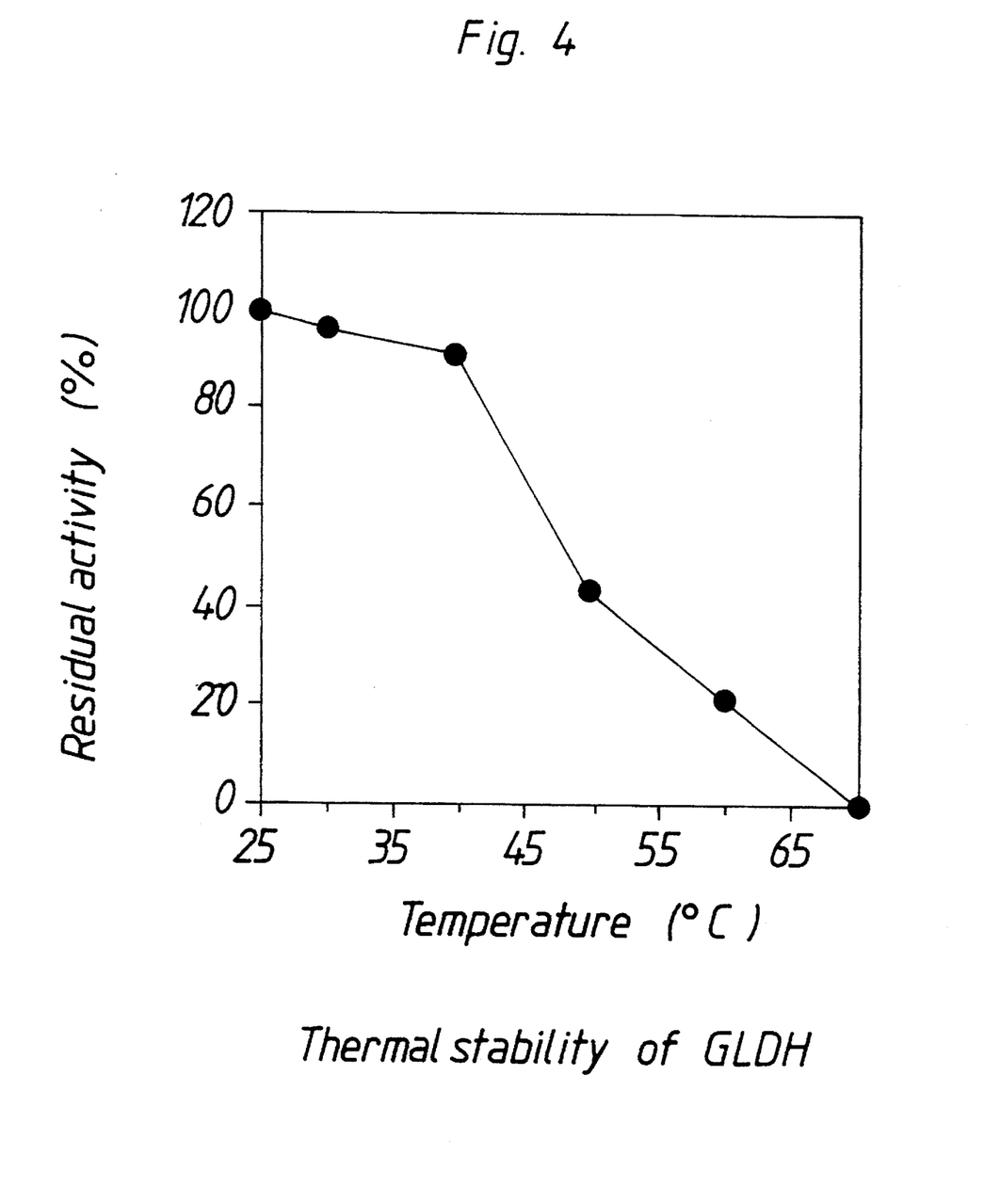
FIG. 4 is a graph showing the temperature stability.

The enzyme according to the present invention was incubated in a 50 mM K-phosphate buffer solution (pH 7.0) for 10 minutes, after which the residual activity was measured. The results were as shown in FIG. 4, and the stability was confirmed up to 30° C. inclusive.

(8) Absorption spectra

Figure 5:
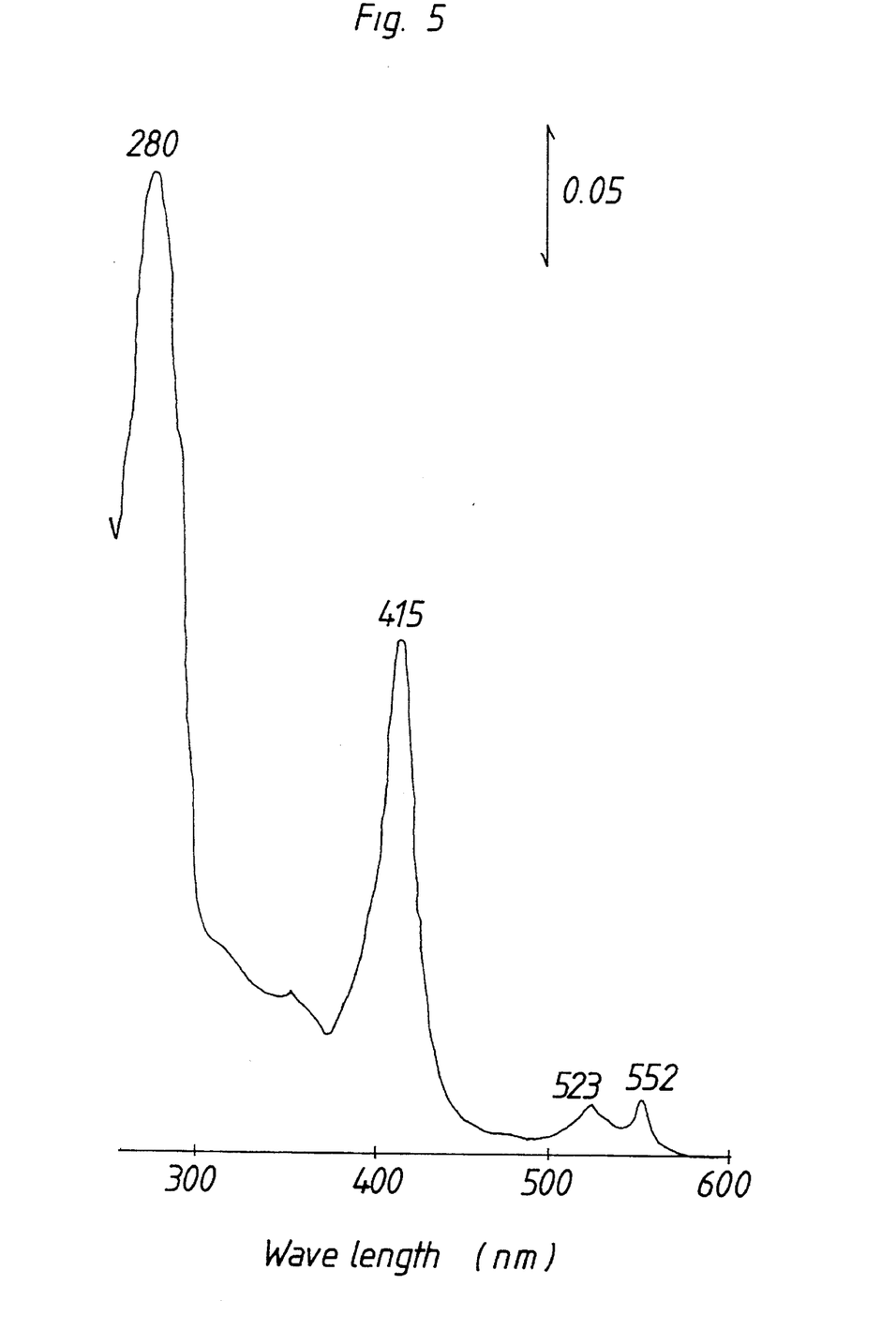
FIG. 5 is a drawing showing the absorbance spectra of the enzyme according to the present invention.

The purified enzyme showed specific absorption at 280, 415, 523 and 552 nm (FIG. 5).

(9) Prosthetic group

Analysis by pyridine-hemochromogen spectra of the enzyme according to the present invention showed that the enzyme contained one molecule of cytochrome C per molecule. Further, enzymatic quantitative determination of the content of free PQQ, a product resulting from the treatment of the enzyme with an organic solvent, revealed that one molecule of the enzyme contained one molecule of PQQ.

(10) Molecular weight

The molecular weight was about 70,000 by analysis according to gel filtration using Sephadex G-200. Also the result of SDS-PAGE proved the molecular weight to be about 70,000.

COMPARISON 1

*Gluconobacter industrious* IFO3260 was cultivated in the same manner as in Example 1. The culture solution was centrifuged to harvest the cells which were then subjected to a conventional manner to yield a membrane fraction. This membrane fraction was suspended in a 50 mM Tris-HCl buffer solution (pH 8.0), and 0.1% dimethyldodecylamine oxide was added thereto to 0.5% concentration, followed by stirring for 60 minutes and extraction. The resulting enzyme solution was fractionated by PEG6000, thereby providing an enzyme preparation having a specific activity of 26 U/mg.

The obtained glycerol dehydrogenase had the following properties:

(1) It catalyzed the following reaction:

Glycerol+Electron Acceptor→Glyceraldehyde+

Reduced Electron Acceptor (2) Electron acceptor

It utilized potassium ferricyanide, 2,6-dichlorophenolindophenol, Wurster's blue, nitrotetrazolium blue, etc.

(3) Km value

The Km value for glycerol was 34 mM.

(4) Stability

The instant enzyme was stable in the presence of 0.1% dimethyldodecylamine oxide and 10% glycerol, and lost its activity rapidly upon removal of them.

(5) Prosthetic group

The enzyme was treated with a solvent to release a prosthetic group which was then identified according to enzymatic quantitative determination to reveal that it comprised PQQ.

EXAMPLE 2

Figure 6:
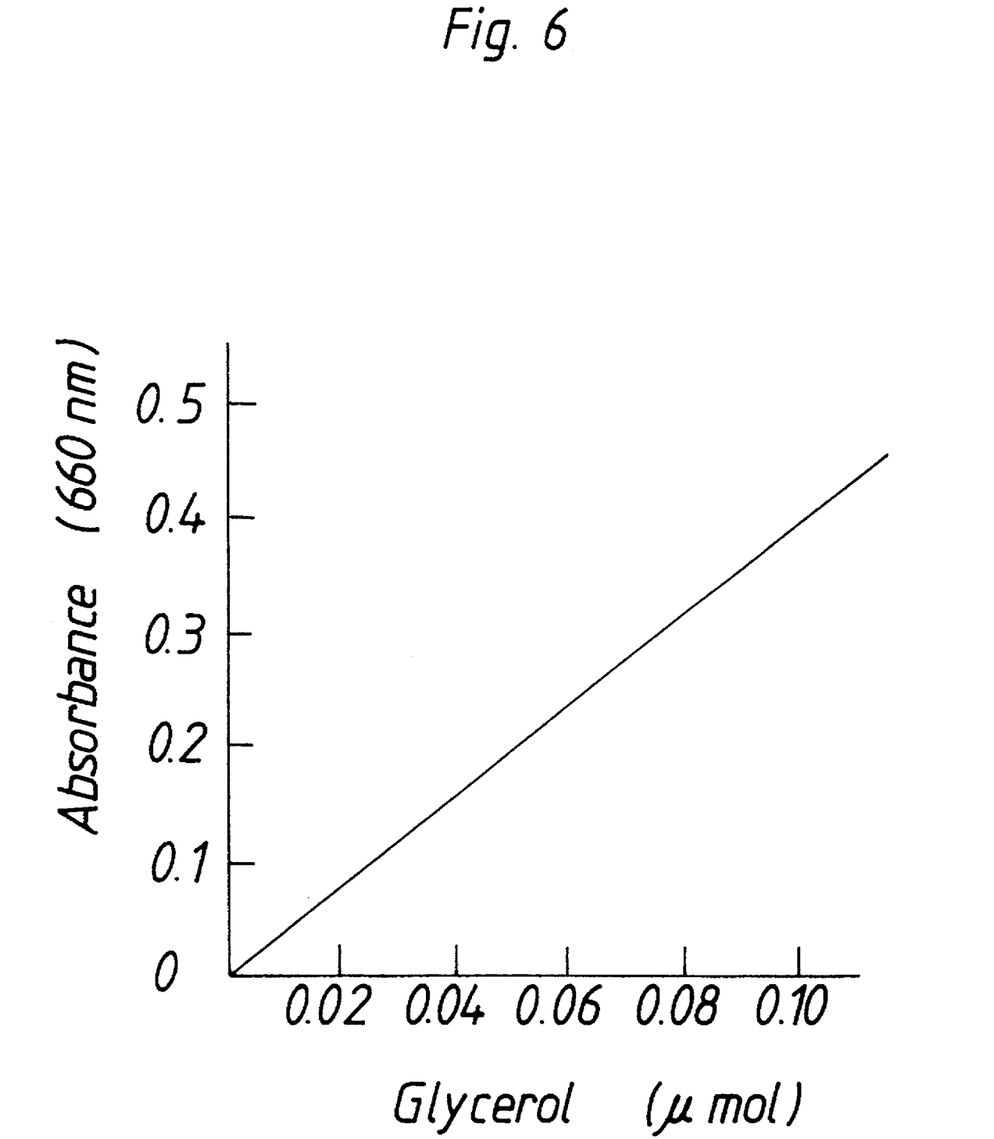
FIG. 6 is a calibration curve for glycerol.

Six sample solutions were prepared which contained 0.01, 0.02, 0.04, 0.06, 0.08 and 0.10 mm of glycerol, respectively. Zero point eight liters of an enzyme solution was added to 0.1 ml of each of these solutions to a total volume of 0.9 ml. The mixture was allowed to stand at 25° C. for 5 minutes, and 0.1 ml of a potassium ferricyanide solution was added thereto for the initiation of the reaction. The reaction was carried out at 25° C. for 20 minutes, and was terminated by the addition of 0.5 ml of ferric sulfate/Dupanol reagent, a reaction terminating solution. To this reaction mixture was added 3.5 ml of distilled water, after which the mixture was allowed to stand at 25° C. for 30 minutes. Determination of the absorbance at 660 nm was conducted with a spectrophotometer, and the results were as shown in FIG. 6; the glycerol content increased linearly within the range of 0.01–0.1 μm, and thus quantitative determination thereof was possible.

COMPARISON 2

Six glycerol sample solutions were prepared in the same manner as in Example 2. To each of these solutions was added 0.8 ml of a solution of the enzyme produced by the Gluconobacter industrius IFO 3260, to a total volume of 0.9 ml. The mixture was allowed to stand at 25° C. for 5 minutes, and 0.1 ml of a potassium ferricyanide solution was added thereto for the initiation of the reaction. The reaction was carried out at 25° C. for 20 minutes, and was terminated by the addition of 0.5 ml of ferric sulfate/Dupanol reagent, a reaction terminating solution. To this reaction mixture was added 3.5 ml of distilled water, after which the mixture was allowed to stand at 25° C. for 30 minutes. Determination was conducted of the absorbance at 660 nm with a spectrophotometer. Due to the absence of 0.1% dimethyldodecylamine oxide and 10% glycerol as the stabilizers the enzyme was deactivated, resulting in failure in the quantitative determination of glycerol. The same deactivation of the enzyme and failure in the glycerol determination were also observed for a system comprising 0.1% dimethyldodecylamine oxide as the sole stabilizer.

PQQ-dependent glycerol dehydrogenase is provided according to the present invention which does not require the use of any surfactant for its solubilization and stability. Use of this enzyme makes it possible to carry out the quantitative determination of glycerol in a cheap and simple manner, without use of an expensive coenzyme.

What is claimed is:

1. A method for quantitative determination of glycerol in a sample which comprises mixing a sample with a glycerol dehydrogenase produced by Pseudomonas sp. TE 3493 which produces glyceraldehyde from glycerol and which:

(a) catalyzes the reaction:

glycerol+electron acceptor →glyceraldehyde+reduced electron acceptor, (b) has an optimum pH in the range of pH 8–9, (c) has a pH stability range of pH 7–11, (d) has an optimum temperature range of 20°–25° C, (e) has a thermal stability of 10 minutes at a pH of 7.0 at a temperature of 30° C. or less, (f) has a molecular weight of 70,000 based on gel filtration and SDS polyacrylamide gel electrophoresis, (g) binds to pyrroloquinoline quinone as a prosthetic group, and (h) is soluble and stable in the absence of ionic or non-ionic surfactants, in the presence of an electron acceptor, and measuring the difference in absorbance of the electron acceptor.

2. The method as claimed in claim 1, wherein the electron acceptor is selected from the group consisting of a ferricyanide, a combination of an electron carrier and 2,6-dichlorophenolindophenol, and a combination of an electron carrier and tetrazolium salt.

3. The method as claimed in claim 2, wherein the ferricyanide is potassium ferricyanide.

4. The method as claimed in claim 2, wherein the electron carrier is selected from the group consisting of phenazine methosulfate, 1-methoxy-5-methylphenazonium methylsulfate, and 9-dimethylaminobenzo-α-phenazoxonium chloride.

5. The method as claimed in claim 2, wherein the tetrazolium salt is selected from the group consisting of nitrotetrazolium blue, 3-(p-iodophenyl)-2-(p-nitrophenyl)-5- phenyl-2H tetrazolium chloride, 3-(4,5-dimethyl)-2-thioazolyl)2,5-dopenyl-2H tetrazolium bromide, neotetrazolium blue, tetranitrotetrazolium blue, and tetrazolium blue.

6. A method for quantitative determination of neutral fat in a sample which comprises mixing a sample with a lipoprotein lipase to decompose the neutral fat in the sample into free fatty acid and glycerol, reacting the glycerol with a glycerol dehydrogenase produced by Pseudomonas sp. TE 3493 which produces glyceraldehyde from glycerol and which:

(a) catalyzes the reaction:

glycerol+electron acceptor→glyceraldehyde+reduced electron acceptor, (b) has an optimum pH in the range of pH 8–9,
(c) has a pH stability range of pH 7–11,
(d) has an optimum temperature range of 20°–25° C.,
(e) has a thermal stability of 10 minutes at a pH of 7.0 at a temperature of 30° C. or less,
(f) has a molecular weight of 70,000 based on gel filtration and SDS polyacrylamide gel electrophoresis,
(g) binds to pyrroloquinoline quinone as a prosthetic group, and
(h) is soluble and stable in the absence of ionic or non-ionic surfactants, in the presence of an electron acceptor; and measuring the difference in absorbance of the electron acceptor.

* * * * *